(12) United States Patent
Kazanchyan et al.

(10) Patent No.: US 11,986,473 B2
(45) Date of Patent: *May 21, 2024

(54) PREVENTION AND/OR TREATMENT OF CONTRAST-INDUCED ACUTE KIDNEY INJURY

(71) Applicant: Saghmos Therapeutics, Inc., Greenwich, CT (US)

(72) Inventors: Anna Kazanchyan, Weston, CT (US); Shalini Cornelio, Holmdel, NJ (US)

(73) Assignee: Saghmos Therapeutics, Inc., Greenwich, CT (US)

(*) Notice: Subject to any disclaimer, the term of this patent is extended or adjusted under 35 U.S.C. 154(b) by 245 days.

This patent is subject to a terminal disclaimer.

(21) Appl. No.: 17/475,212

(22) Filed: Sep. 14, 2021

(65) Prior Publication Data

US 2021/0401832 A1 Dec. 30, 2021

Related U.S. Application Data

(63) Continuation of application No. 16/462,789, filed as application No. PCT/US2017/062771 on Nov. 21, 2017, now Pat. No. 11,123,345.

(60) Provisional application No. 62/424,771, filed on Nov. 21, 2016.

(51) Int. Cl.
*A61K 31/495* (2006.01)
*A61P 13/12* (2006.01)

(52) U.S. Cl.
CPC ............ *A61K 31/495* (2013.01); *A61P 13/12* (2018.01)

(58) Field of Classification Search
CPC .............................. A61K 31/495; A61P 13/12
See application file for complete search history.

(56) References Cited

U.S. PATENT DOCUMENTS

| | | | |
|---|---|---|---|
| 4,407,801 A | 10/1983 | Arnaud | |
| 2008/0059228 A1 | 3/2008 | Bossi | |
| 2009/0257999 A1 | 10/2009 | Fink | |
| 2010/0266501 A1 | 10/2010 | Meyer et al. | |
| 2011/0048980 A1 | 3/2011 | Seman | |
| 2013/0202710 A1 | 8/2013 | Genty et al. | |
| 2013/0302290 A1 | 11/2013 | Amrani et al. | |
| 2015/0353602 A1 | 12/2015 | Szeto et al. | |
| 2016/0081961 A1 | 3/2016 | Cushing | |
| 2018/0140599 A1 | 5/2018 | Kazanchyan et al. | |
| 2018/0190374 A1 | 7/2018 | Kazanchyan et al. | |
| 2019/0156929 A1 | 5/2019 | Kazanchyan et al. | |

FOREIGN PATENT DOCUMENTS

| WO | WO-2009/034541 | 3/2009 |
|---|---|---|
| WO | WO-2009/066315 | 5/2009 |
| WO | WO-2018/094387 | 5/2018 |
| WO | WO-2018/129045 | 7/2018 |

OTHER PUBLICATIONS

Chawla et al., "Acute kidney disease and renal recovery: consensus report of the Acute Disease Quality Initiative (ADQI) 16 Workgroup," *Nature Reviews* (2017) 13:241.

Chen et al., "Coenzyme Q10 combined with trimetazidine in the prevension of contrast-induced nephropathy in patients with coronary heart disease complicated with renal dysfunction undergoing elective cardiac catheterization: a randomized control study and in vivo study," European Journal of Medical Research (2018), vol. 23, No. 23; pp. 1-10.

European Search Report dated Apr. 24, 2020, corresponding to European Application No. 17872053.8, 7 pages.

Filho et al., "Trimetazidine as cardioplegia addictive without pretreatment does not improve myocardial protection: study in a swine working heart model," *Rev. Bras Cir. Cardiovasc.* (2008) 23(2):224-234.

Fu et al., "Trimetazidine can prevent the occurrence of contrast-induced nephropathy after percutaneous coronary intervention in elderly patients with renal insufficiency," *Research Article* (2020) 2 pages.

Hadi et al., "Impact of Trimetazidine on Incidence of Contrast Induced Nephropathy in Diabetic Patients with Renal Insufficiency Undergoing Percutaneous Coronary Intervention," *Sys Rev Pharm* (2020) 11(2):329-341.

Ibrahim et al., "Trimetazidine in the prevention of contrast-induced nephropathy in chronic kidney disease," (2017) 18(5):315-319.

International Search Report and Written Opinion, dated Jan. 24, 2018, corresponding to International Patent Application No. PCT/US17/62771; 12 total pages.

International Search Report and Written Opinion, dated Mar. 26, 2018, corresponding to International Patent Application No. PCT/US18/012187; 7 total pages.

Labrou et al., Original Research Article, "Trimetazidine Administration Minimizes Myocardial Damage and Improves 7 e-eft Ventricular Function after Percutaneous Coronary Intervention," Am. J. Cardiovasc Drugs (2007); vol. 7, No. 2; pp. 143-150.

Lian et al., "The effect of trimetazidine on preventing contrast-induced nephropathy after cardiac catheterization," *International Urology and Nephrology* (2019) 51:2267-2272.

Liu et al. "Trimetazidine Prevention of Contrast-Induced Nephropathy in Coronary Angiography", Clinical Investigation, The American Journal of the Medical Sciences, vol. 350, No. 5, Nov. 2015; pp. 398-402.

(Continued)

*Primary Examiner* — Savitha M Rao
(74) *Attorney, Agent, or Firm* — MORRISON & FOERSTER LLP

(57) ABSTRACT

Methods are provided for preventing, reducing, and/or treating contrast-induced acute kidney injury which include administering an inhibitor of fatty acid oxidation to a patient in need thereof. Also provided are methods involving use of trimetazidine or pharmaceutically acceptable salts thereof for the prevention and/or treatment of contrast-induced acute kidney injury. Methods are also provided for preventing and/or treating contrast-induced acute kidney injury which include administration of one or more of trimetazidine, etomoxir, oxfenicine, perhexiline, mildronate, or ranolazine, or pharmaceutically acceptable salts of any of the preceding.

13 Claims, No Drawings

(56) References Cited

OTHER PUBLICATIONS

McCarthy et al., "The role of trimetazidine in cardiovascular disease: beyond an anti-anginal agent," European Heart Journal—Cardiovascular Pharmacotherapy (2016), vol. 2; pp. 266-272.

Onbasili et al., "Trimetazidine in the prevention of contrast-induced nephropathy after coronary procedures", Interventional Cardiology, Heart, 2007, vol. 93; pp. 698-702.

Rahman et al., "Trimetazidine in the Prevention of Contrast Induced Nephropathy after Coronary Angiogram", Mymensingh Med J. Apr. 2012, vol. 21, No. 2; pp. 292-299.

Shehata, "Impact of Trimetazidine on Incidence of Myocardial Injury and Contrast-Induced Nephropathy in Diabetic 4 Patients With Renal Dysfunction Undergoing Elective Percutaneous Coronary Intervention", The American Journal of Cardiology 2014, vol. 114; pp. 389-394.

PREVENTION AND/OR TREATMENT OF CONTRAST-INDUCED ACUTE KIDNEY INJURY

CROSS-REFERENCE TO RELATED APPLICATIONS

This application is a continuation of U.S. patent application Ser. No. 16/462,789, having an international filing date of Nov. 17, 2017, now allowed, which is a national stage filing of PCT/US2017/062771, filed Nov. 17, 2017, which claims the benefit of and priority to U.S. Provisional Application No. 62/424,771, Nov. 21, 2016, the disclosures of each of these applications are hereby incorporated herein by reference in their entirety.

TECHNICAL FIELD

Methods of preventing contrast-induced acute kidney injury by administering an inhibitor of fatty acid oxidation to a patient in need thereof.

BACKGROUND OF THE INVENTION

Contrast-induced acute kidney injury (CI-AKI) (also known as contrast-induced nephropathy) is an abrupt deterioration in renal function that can be associated with use of contrast medium. A contrast medium (or contrast agent) is a substance used to enhance the contrast of structures or fluids within the body in medical imaging. Kidney injury may be associated with a sharp decrease in kidney function over a period of 48-72 hours, potentially leading to chronic kidney injury, increased mortality, infarction/re-infarction and higher rates of major adverse cardiovascular events (MACE) over 1 year. The symptoms can be similar to those of kidney disease, which include feeling more tired, poor appetite, swelling in the feet and ankles, puffiness around the eyes, or dry and itchy skin. In some cases, this can lead to serious kidney problems and possible heart and blood vessel problems.

A number of therapies for kidney injury have been investigated, including the use of statins, bicarbonate, N-acetylcysteine, ascorbic acid, theophylline and aminophylline, vasodilators, forced diuresis, and renal replacement therapy. Trimetazidine (1-2,3,4-trimethoxybenzyl)piperazine) has been used for angina pectoris and has been marketed outside of the United States in over 90 countries for over 35 years. Trimetazidine, however, has never been approved in the United States for any indication. It was developed by Les Laboratoires Servier (France) and was first authorized in France in 1978. Three pharmaceutical forms are available in Europe: 20 mg tablet, 20 mg/ml oral solution and 35 mg modified release tablets (MR) under the brand names Vastarel® and Vastarel MR®, and is also available as a generic or branded generic with various names in over 90 countries. Trimetazidine has been described as the first cytoprotective anti-ischemic agent that improves myocardial glucose utilization through inhibition of fatty acid metabolism. Trimetazidine has been tested for the prevention of contrast-induced nephropathy in patients, e.g., with high serum creatinine levels undergoing coronary angiography/angioplasty. For example, four investigator—sponsored Phase 2 clinical trials have tested trimetazidine for prevention of CI-AKI. Results of these trials were published in peer-reviewed journals and demonstrated that trimetazidine was more effective than isotonic saline in reducing the risk of contrast-induced nephropathy (CIN). See Onbasili A O, et al., HEART, 2007. 93:698-702, Rahman M M, et al., MYMENSINGH MED J, 2012. 21(2):292-299, Shehata M, Am. J Cardiol, 2014. 114:389-394, and Liu W, et al., Am. J. Med Sci, 2015. 350:398-402. However, contrast-induced acute kidney injury (CI-AKI) remains a significant unmet medical need and there remains a need for improved methods of preventing contrast-induced acute kidney injury.

BRIEF SUMMARY OF THE INVENTION

In embodiments, methods are provided for preventing, reducing the incidence of, and/or treating contrast-induced acute kidney injury which include administering to a patient in need thereof an inhibitor of fatty acid oxidation. In embodiments, methods are provided for preventing, reducing, and/or treating contrast-induced acute kidney injury including administering to a patient in need thereof trimetazidine or a pharmaceutically acceptable salt thereof. For example, methods are provided for preventing contrast-induced acute kidney injury in a patient undergoing a cardiac procedure that requires administration of contrast media for imaging. In embodiments, methods are provided for preventing, reducing, and/or treating contrast-induced acute kidney injury including administering to a patient in need thereof trimetazidine or a pharmaceutically acceptable salt thereof in an amount of more than 20 mg. In embodiments, methods are provided for preventing, reducing, and/or treating contrast-induced acute kidney injury including administering to a patient in need thereof trimetazidine or a pharmaceutically acceptable salt thereof in an amount of more than 35 mg. In embodiments, methods are provided for preventing, reducing, and/or treating contrast-induced acute kidney injury which include administering to a patient in need thereof trimetazidine or a pharmaceutically acceptable salt thereof in combination with etomoxir, oxfenicine, perhexiline, mildronate, or ranolazine or a pharmaceutically acceptable salt of any of the preceding. In embodiments, methods are provided for preventing, reducing, and/or treating contrast-induced acute kidney injury which include administering to a patient in need thereof etomoxir, oxfenicine, perhexiline, mildronate, or ranolazine or a pharmaceutically acceptable salt of any of the preceding. In embodiments, methods are provided for preventing, reducing, and/or treating contrast-induced acute kidney injury which include administering to a patient in need thereof one or more of trimetazidine, etomoxir, oxfenicine, perhexiline, mildronate, ranolazine or a pharmaceutically acceptable salt of any of the preceding.

In embodiments, the patient is administered an inhibitor of fatty acid oxidation prior to undergoing a cardiac procedure. In embodiments, the patient is administered trimetazidine etomoxir, oxfenicine, perhexiline, mildronate, or ranolazine or a pharmaceutically acceptable salt of any of the preceding, prior to undergoing a cardiac procedure. In embodiments, the patient is administered trimetazidine or a pharmaceutically acceptable salt thereof prior to undergoing a cardiac procedure. For example, the patient may be administered trimetazidine or a pharmaceutically acceptable salt thereof for more than, e.g., 24, 48, or 72 hours, prior to undergoing a cardiac procedure. In other examples, the patient in need thereof is administered trimetazidine or a pharmaceutically acceptable salt thereof for at least 96 hours prior to undergoing a cardiac procedure. In embodiments, trimetazidine or a pharmaceutically acceptable salt thereof may be administered once a day. In embodiments, trimetazidine or a pharmaceutically acceptable salt thereof may be administered twice daily. In embodiments, trimetazidine or a pharmaceutically acceptable salt thereof may be administered three times daily. In embodiments, the trimetazidine or a pharmaceutically acceptable salt thereof may be administered four times daily.

In embodiments, the patient is administered etomoxir, oxfenicine, perhexiline, mildronate, or ranolazine or a pharmaceutically acceptable salt of any of the preceding, prior to undergoing a cardiac procedure. For example, the patient may be administered etomoxir, oxfenicine, perhexiline, mildronate, or ranolazine or a pharmaceutically acceptable salt of any of the preceding, for more than, e.g., 24, 48, or 72 hours, prior to undergoing a cardiac procedure. In other examples, the patient in need thereof is administered etomoxir, oxfenicine, perhexiline, mildronate, or ranolazine or a pharmaceutically acceptable salt of any of the preceding, for at least 96 hours prior to undergoing a cardiac procedure. In embodiments, etomoxir, oxfenicine, perhexiline, mildronate, or ranolazine or a pharmaceutically acceptable salt of any of the preceding, may be administered once, twice, three or four times a day. In embodiments, trimetazidine or a pharmaceutically acceptable salt thereof can be administered with at least one of etomoxir, oxfenicine, perhexiline, mildronate, or ranolazine or a pharmaceutically acceptable salt of any of the preceding.

In embodiments, the patient may be administered an inhibitor of fatty acid oxidation for more than, e.g., 30, 45, 60, 75, or 90 days, after undergoing a cardiac procedure. In embodiments, the patient may be administered trimetazidine or a pharmaceutically acceptable salt thereof for more than, e.g., 30, 45, 60, 75, or 90 days, after undergoing a cardiac procedure. For example, the patient may be administered trimetazidine or a pharmaceutically acceptable salt thereof twice daily for more than 60 days after undergoing a cardiac procedure. In other examples, the patient may be administered trimetazidine or a pharmaceutically acceptable salt thereof twice daily for a total of 90 days. In embodiments, the patient may be administered etomoxir, oxfenicine, perhexiline, mildronate, or ranolazine or a pharmaceutically acceptable salt of any of the preceding, for more than, e.g., 30, 45, 60, 75, or 90 days, after undergoing a cardiac procedure, e.g., a computed tomography (CT) scan. For example, the patient may be administered etomoxir, oxfenicine, perhexiline, mildronate, or ranolazine or a pharmaceutically acceptable salt of any of the preceding, twice daily for more than 60 days after undergoing a cardiac procedure. In other examples, the patient may be administered etomoxir, oxfenicine, perhexiline, mildronate, or ranolazine or a pharmaceutically acceptable salt of any of the preceding, twice daily for a total of 90 days.

In embodiments, the patient may be administered an inhibitor of fatty acid oxidation three times daily for more than 48 hours prior to undergoing a cardiac procedure and administered trimetazidine or a pharmaceutically acceptable salt thereof twice daily for more than 60 days after undergoing the cardiac procedure. In embodiments, the patient may be administered trimetazidine or a pharmaceutically acceptable salt thereof three times daily for more than 48 hours prior to undergoing a cardiac procedure and administered trimetazidine or a pharmaceutically acceptable salt thereof twice daily for more than 60 days after undergoing the cardiac procedure. In embodiments, the patient may be administered etomoxir, oxfenicine, perhexiline, mildronate, or ranolazine or a pharmaceutically acceptable salt of any of the preceding, three times daily for more than 48 hours prior to undergoing a cardiac procedure and administered trimetazidine or a pharmaceutically acceptable salt thereof twice daily for more than 60 days after undergoing the cardiac procedure.

In embodiments, methods of preventing, reducing, and/or treating contrast-induced acute kidney injury include parenterally administering an inhibitor of fatty acid oxidation to a patient within 6 hours prior to administering a contrast agent to the patient. In embodiments, methods of preventing, reducing, and/or treating contrast-induced acute kidney injury include parenterally administering an inhibitor of fatty acid oxidation to a patient within 5, 4, 3, 2 or 1 hour(s) prior to administering a contrast agent to the patient. In embodiments, methods of preventing, reducing, and/or treating contrast-induced acute kidney injury include parenterally administering trimetazidine or a pharmaceutically acceptable salt thereof to a patient within 6 hours prior to administering a contrast agent to the patient. In embodiments, methods of preventing, reducing, and/or treating contrast-induced acute kidney injury include parenterally administering trimetazidine or a pharmaceutically acceptable salt thereof to a patient within 5, 4, 3, 2 or 1 hour(s) prior to administering a contrast agent to the patient. In embodiments, methods of preventing, reducing, and/or treating contrast-induced acute kidney injury include parenterally administering one or more of etomoxir, oxfenicine, perhexiline, mildronate, or ranolazine or a pharmaceutically acceptable salt of any of the preceding, to a patient within 6 hours prior to administering a contrast agent to the patient. In embodiments, methods of preventing, reducing, and/or treating contrast-induced acute kidney injury include parenterally administering one or more of etomoxir, oxfenicine, perhexiline, mildronate, or ranolazine or a pharmaceutically acceptable salt of any of the preceding, to a patient within 5, 4, 3, 2 or 1 hour(s) prior to administering a contrast agent to the patient. In embodiments, methods of preventing, reducing, and/or treating contrast-induced acute kidney injury include parenterally administering trimetazidine or a pharmaceutically acceptable salt thereof in combination with one or more of etomoxir, oxfenicine, perhexiline, mildronate, or ranolazine or a pharmaceutically acceptable salt of any of the preceding, to a patient within 6 hours prior to administering a contrast agent to the patient. In embodiments, methods of preventing, reducing, and/or treating contrast-induced acute kidney injury include parenterally administering trimetazidine or a pharmaceutically acceptable salt thereof in combination with one or more of etomoxir, oxfenicine, perhexiline, mildronate, or ranolazine or a pharmaceutically acceptable salt of any of the preceding, to a patient within 5, 4, 3, 2 or 1 hour(s) prior to administering a contrast agent to the patient. In embodiments, the parenteral administration is intravenous administration.

In embodiments, methods are provided for preventing contrast-induced acute kidney injury including administering to a patient in need thereof trimetazidine or a pharmaceutically acceptable salt thereof wherein the composition provides an in vivo plasma profile having a $C_{max}$ more than about 65 μg/ml.

In embodiments, methods are provided for preventing contrast-induced acute kidney injury including administering to a patient in need thereof trimetazidine or a pharmaceutically acceptable salt thereof wherein the composition provides an in vivo plasma profile having an AUC more than about 500 μg hr/ml.

In embodiments, provided herein are methods for preventing, reducing, and/or treating contrast-induced acute kidney injury by administering to a patient in need thereof an effective amount of an inhibitor of fatty acid oxidation before, during and after procedures involving use of devices such as guide wires and intracoronary pressure wires, cardiac catheters, atherectomy devices, intracoronary stents, thrombus extraction catheters, embolic protection devices, replacement cardiac valves and/or vascular closure devices. In embodiments, provided herein are methods for preventing, reducing, and/or treating contrast-induced acute kidney injury by administering to a patient in need thereof an effective amount of trimetazidine or pharmaceutically acceptable salt thereof before, during and after procedures involving use of devices such as guide wires and intracoronary pressure wires, cardiac catheters, atherectomy devices, intracoronary stents, thrombus extraction catheters, embolic protection devices, replacement cardiac valves and/or vascular closure devices. In embodiments, provided herein are methods for preventing, reducing, and/or treating contrast-induced acute kidney injury by administering to a patient in need thereof an effective amount of etomoxir, oxfenicine, perhexiline, mildronate, or ranolazine or a pharmaceutically acceptable salt of any of the preceding, before, during and after procedures involving use of devices such as guide wires and intracoronary pressure wires, cardiac catheters, atherectomy devices, intracoronary stents, thrombus extraction catheters, embolic protection devices, replacement cardiac valves and/or vascular closure devices.

In embodiments, provided herein are methods for preventing, reducing, and/or treating contrast-induced acute kidney injury by administering to a patient in need thereof an effective amount an inhibitor of fatty acid oxidation in combination with or before and after administration of contrast media, anticoagulants, and anti-platelet agents. In embodiments, provided herein are methods for preventing, reducing, and/or treating contrast-induced acute kidney injury by administering to a patient in need thereof an effective amount of trimetazidine or pharmaceutically acceptable salt thereof in combination with or before and after administration of contrast media, anticoagulants, and anti-platelet agents. In embodiments, provided herein are methods for preventing, reducing, and/or treating contrast-induced acute kidney injury by administering to a patient in need thereof an effective amount etomoxir, oxfenicine, perhexiline, mildronate, or ranolazine or a pharmaceutically acceptable salt of any of the preceding, in combination with or before and after administration of contrast media, anticoagulants, and anti-platelet agents.

DETAILED DESCRIPTION OF THE INVENTION

Described herein are methods of preventing, reducing, and/or treating contrast-induced acute kidney injury including administering to a patient in need thereof an inhibitor of fatty acid oxidation. Described herein are methods of preventing, reducing, and/or treating contrast-induced acute kidney injury including administering to a patient in need thereof trimetazidine or a pharmaceutically acceptable salt thereof. Described herein are methods of preventing, reducing, and/or treating contrast-induced acute kidney injury including administering to a patient in need thereof etomoxir, oxfenicine, perhexiline, mildronate, or ranolazine or a pharmaceutically acceptable salt of any of the preceding. Described herein are methods of reducing the incidence of contrast-induced acute kidney injury including administering to a patient in need thereof one or more of trimetazidine, etomoxir, oxfenicine, perhexiline, mildronate, or ranolazine or a pharmaceutically acceptable salt of any of the preceding. Described herein are methods of reducing the incidence of contrast-induced acute kidney injury including administering to a patient in need thereof trimetazidine or a pharmaceutical salt thereof, in combination with one or more of etomoxir, oxfenicine, perhexiline, mildronate, or ranolazine or a pharmaceutically acceptable salt of any of the preceding.

Provided are methods of preventing, reducing, and/or treating contrast-induced acute kidney injury including administering to a patient in need thereof trimetazidine or a pharmaceutically acceptable salt thereof. In embodiments, methods of preventing the progression of acute kidney injury (AKI) to a chronic kidney disease (CKD) is provided. In embodiments, methods are provided for prevention of contrast-induced acute kidney injury by administering to a patient trimetazidine or a pharmaceutically acceptable salt thereof. In embodiments, methods of reducing contrast-induced acute kidney injury are provided. In some embodiments, reduction and/or prevention of Major Adverse Renal and Cardiac Events (MARCE) in subjects undergoing coronary angiography are provided. Provided are methods for reducing the incidence of a Major Adverse Renal and Cardiac Event in subjects with impaired renal function by administering to a patient trimetazidine or a pharmaceutically acceptable salt thereof. In some embodiments, methods for the reduction and/or prevention of contrast-induced acute kidney injury in subjects undergoing coronary angiography by administering to a patient trimetazidine or a pharmaceutically acceptable salt thereof are provided. In some embodiments, provided are methods for the reduction and/or prevention of contrast-induced acute kidney injury in subjects undergoing coronary angiography for Acute Coronary Syndrome (ACS) by administering to a patient trimetazidine or a pharmaceutically acceptable salt thereof.

In some embodiments, methods are provided for the reduction and/or prevention of contrast-induced acute kidney injury in subjects with impaired renal function by administering to a patient trimetazidine or a pharmaceutically acceptable salt thereof. In other embodiments, methods for the reduction and/or prevention of contrast-induced acute kidney injury in subjects undergoing coronary angiography for Acute Coronary Syndrome (ACS), excluding ST elevation Myocardial Infarction (STEMI) by administering to a patient trimetazidine or a pharmaceutically acceptable salt thereof are provided. In some embodiments, methods are provided for the reduction and/or prevention of contrast-induced acute kidney injury in subjects undergoing coronary angiography for Acute Coronary Syndrome (ACS), excluding ST elevation Myocardial Infarction (STEMI) with impaired renal function by administering to a patient trimetazidine or a pharmaceutically acceptable salt thereof. In some embodiments, methods are provided for the reduction and/or prevention of Major Adverse Renal and Cardiac Events in subjects undergoing coronary angiography for Acute Coronary Syndrome (ACS), excluding ST elevation Myocardial Infarction (STEMI) with impaired renal function by administering to a patient trimetazidine or a pharmaceutically acceptable salt thereof. In some embodiments, methods for reduction of risk of CI-AKI and associated MARCE in subjects undergoing coronary angiography for ACS are provided.

In some embodiments, methods are provided for the reduction and/or prevention of contrast-induced acute kidney injury in subjects with impaired renal function by administering to a patient trimetazidine or a pharmaceutically acceptable salt thereof. In some embodiments, methods for the reduction and/or prevention of contrast-induced acute kidney injury in subjects with impaired renal function by administering to a patient 60 mg trimetazidine or a pharmaceutically acceptable salt thereof are provided. In some embodiments, methods are provided for the reduction and/or prevention of contrast-induced acute kidney injury in subjects with impaired renal function by administering to a patient more than 40 mg trimetazidine or a pharmaceutically acceptable salt thereof. For example, the methods may include administering to a patient more than 40 mg trimetazidine in a single day administered in one or more dosages. In some embodiments, methods are provided for the reduction and/or prevention of contrast-induced acute kidney injury in subjects with impaired renal function by administering to trimetazidine or a pharmaceutically acceptable salt thereof three times daily. In some embodiments, methods are provided for the reduction and/or prevention of contrast-induced acute kidney injury in subjects with impaired renal function by administering to trimetazidine or a pharmaceutically acceptable salt thereof 20 mg three times daily. In some embodiments patients administered trimetazidine according the disclosed methods may have an estimated glomerular filtration rate (eGFR) of <45 mL/min and >15 mL/min as determined by the Modification of Diet in Renal Disease (MDRD) equation. In some embodiments patients administered trimetazidine according the disclosed methods may have an eGFR <60 mL/min and >15 mL/min as determined by the MDRD equation.

Many pharmaceutical products are administered as a fixed dose, at regular intervals, to achieve therapeutic efficacy. Its duration of action is reflected by its plasma half-life. Since efficacy is often dependent on sufficient exposure administration may require frequent maintenance dosing. Advantageously disclosed herein are methods of preventing contrast-induced acute kidney injury by administration of trimetazidine or pharmaceutically acceptable salt thereof. For example, in embodiments, methods of treating a contrast-induced acute kidney injury are provided which include administering to a patient in need thereof a pharmaceutical composition including about 20 mg to about 200 mg of trimetazidine or pharmaceutically acceptable salt thereof.

In embodiments, the patient is administered an inhibitor of fatty acid oxidation prior to undergoing a cardiac procedure. In embodiments, the patient is administered trimetazidine or a pharmaceutically acceptable salt thereof prior to undergoing a cardiac procedure. For example, the patient may be administered trimetazidine or a pharmaceutically acceptable salt thereof for more than, e.g., 24, 48, or 72 hours, prior to undergoing a cardiac procedure. In other examples, the patient is administered trimetazidine or a pharmaceutically acceptable salt thereof for at least 96 hours prior to undergoing a contrast procedure. In some embodiments, the patient is administered trimetazidine or a pharmaceutically acceptable salt thereof for at least 48 hours prior to undergoing a contrast procedure.

In embodiments, trimetazidine or pharmaceutically acceptable salt thereof may be administered once daily. In embodiments, trimetazidine or pharmaceutically acceptable salt thereof may be administered twice daily. In embodiments, trimetazidine or pharmaceutically acceptable salt thereof may be administered three times daily. In embodiments, trimetazidine or pharmaceutically acceptable salt thereof may be administered four times daily. In embodiments, an inhibitor of fatty acid oxidation may be administered once, two, three or four times daily.

In embodiments, the patient may be administered etomoxir, oxfenicine, perhexiline, mildronate, or ranolazine or a pharmaceutically acceptable salt of any of the preceding prior to undergoing a cardiac procedure. For example, the patient may be administered etomoxir, oxfenicine, perhexiline, mildronate, or ranolazine or a pharmaceutically acceptable salt of any of the preceding for more than, e.g., 24, 48, or 72 hours, prior to undergoing a cardiac procedure. In other examples, the patient in need thereof is administered etomoxir, oxfenicine, perhexiline, mildronate, or ranolazine or a pharmaceutically acceptable salt of any of the preceding for at least 96 hours prior to undergoing a cardiac procedure. In embodiments, etomoxir, oxfenicine, perhexiline, mildronate, or ranolazine or a pharmaceutically acceptable salt of any of the preceding may be administered once, two, three or four times daily. In embodiments, trimetazidine or pharmaceutically acceptable salt thereof may be administered in combination with one or more of etomoxir, oxfenicine, perhexiline, mildronate, or ranolazine or a pharmaceutically acceptable salt of any of the preceding. In embodiments, the patient may be administered trimetazidine or a pharmaceutical salt thereof, in combination with one or more of etomoxir, oxfenicine, perhexiline, mildronate, or ranolazine or a pharmaceutically acceptable salt of any of the preceding prior to undergoing a cardiac procedure. For example, the patient may be administered trimetazidine or a pharmaceutical salt thereof, in combination with one or more of etomoxir, oxfenicine, perhexiline, mildronate, or ranolazine or a pharmaceutically acceptable salt of any of the preceding for more than, e.g., 24, 48, or 72 hours, prior to undergoing a cardiac procedure. In other examples, the patient in need thereof is administered trimetazidine or a pharmaceutical salt thereof, in combination with one or more of etomoxir, oxfenicine, perhexiline, mildronate, or ranolazine or a pharmaceutically acceptable salt of any of the preceding for at least 96 hours prior to undergoing a cardiac procedure. In embodiments, trimetazidine or a pharmaceutical salt thereof, in combination with one or more of etomoxir, oxfenicine, perhexiline, mildronate, or ranolazine or a pharmaceutically acceptable salt of any of the preceding may be administered once, two, three or four times daily.

In embodiments, the patient may be administered an inhibitor of fatty acid oxidation for more than, e.g., 30, 45, 60, 75, or 90 days, after undergoing a contrast procedure. In embodiments, the patient may be administered trimetazidine or a pharmaceutically acceptable salt thereof for more than, e.g., 30, 45, 60, 75, or 90 days, after undergoing a cardiac procedure. For example, the patient may be administered trimetazidine or a pharmaceutically acceptable salt thereof twice daily for more than 60 days after undergoing a cardiac procedure. In other examples, the patient may be administered trimetazidine or a pharmaceutically acceptable salt thereof twice daily for a total of 90 days. In embodiments, the patient may be administered etomoxir, oxfenicine, perhexiline, mildronate, or ranolazine or a pharmaceutically acceptable salt of any of the preceding for more than, e.g., 30, 45, 60, 75, or 90 days, after undergoing a contrast procedure. For example, the patient may be administered etomoxir, oxfenicine, perhexiline, mildronate, or ranolazine or a pharmaceutically acceptable salt of any of the preceding twice daily for more than 60 days after undergoing a cardiac procedure. In other examples, the patient may be administered etomoxir, oxfenicine, perhexiline, mildronate, or ranolazine or a pharmaceutically acceptable salt of any of the preceding twice daily for a total of 90 days. In embodiments, trimetazidine or pharmaceutically acceptable salt thereof may be administered in combination with one or more of etomoxir, oxfenicine, perhexiline, mildronate, or ranolazine or a pharmaceutically acceptable salt of any of the preceding for more than, e.g., 30, 45, 60, 75, or 90 days, after undergoing a contrast procedure.

In embodiments, the patient may be administered trimetazidine or a pharmaceutically acceptable salt thereof three times daily for more than 48 hours prior to undergoing a cardiac procedure and administered trimetazidine or a pharmaceutically acceptable salt thereof twice daily for more than 60 days after undergoing the cardiac procedure. In embodiments, the patient may be administered etomoxir, oxfenicine, perhexiline, mildronate, or ranolazine or a pharmaceutically acceptable salt of any of the preceding three times daily for more than 48 hours prior to undergoing a cardiac procedure and administered trimetazidine or a pharmaceutically acceptable salt thereof twice daily for more than 60 days after undergoing the cardiac procedure. In embodiments, trimetazidine or pharmaceutically acceptable salt thereof may be administered in combination with one or more of etomoxir, oxfenicine, perhexiline, mildronate, or ranolazine or a pharmaceutically acceptable salt of any of the preceding.

In embodiments, methods of preventing, reducing, and/or treating contrast-induced acute kidney injury include administering to a patient in need thereof an inhibitor of fatty acid oxidation within 6 hours prior to administration of a contrast agent. In embodiments, methods of preventing, reducing, and/or treating contrast-induced acute kidney injury include administering to a patient in need thereof an inhibitor of fatty acid oxidation within 5, 4, 3, 2 or 1 hour(s) prior to administration of a contrast agent. In embodiments, methods of preventing, reducing, and/or treating contrast-induced acute kidney injury include parenterally administering to a patient in need thereof an inhibitor of fatty acid oxidation within 6 hours prior to administration of a contrast agent. In embodiments, methods of preventing, reducing, and/or treating contrast-induced acute kidney injury include parenterally administering to a patient in need thereof an inhibitor of fatty acid oxidation within 5, 4, 3, 2 or 1 hour(s) prior to administration of a contrast agent. In embodiments, such parenteral administration is intravenous administration.

In embodiments, methods of preventing, reducing, and/or treating contrast-induced acute kidney injury include administering to a patient in need thereof trimetazidine or pharmaceutically acceptable salt thereof, alone or in combination with one or more of etomoxir, oxfenicine, perhexiline, mildronate, or ranolazine or a pharmaceutically acceptable salt of any of the preceding, within 6 hours prior to administration of a contrast agent. In embodiments, methods of preventing, reducing, and/or treating contrast-induced acute kidney injury include administering to a patient in need thereof trimetazidine or pharmaceutically acceptable salt thereof, alone or in combination with one or more of etomoxir, oxfenicine, perhexiline, mildronate, or ranolazine or a pharmaceutically acceptable salt of any of the preceding, within 5, 4, 3, 2 or 1 hour(s) prior to administration of a contrast agent. In embodiments, methods of preventing, reducing, and/or treating contrast-induced acute kidney injury include administering to a patient in need thereof one or more of etomoxir, oxfenicine, perhexiline, mildronate, or ranolazine or a pharmaceutically acceptable salt of any of the preceding, within 6 hours prior to administration of a contrast agent. In embodiments, methods of preventing, reducing, and/or treating contrast-induced acute kidney injury include administering to a patient in need thereof one or more of etomoxir, oxfenicine, perhexiline, mildronate, or ranolazine or a pharmaceutically acceptable salt of any of the preceding, within 5, 4, 3, 2 or 1 hour(s) prior to administration of a contrast agent. In embodiments, methods of preventing, reducing, and/or treating contrast-induced acute kidney injury include parenterally administering to a patient in need thereof one or more of etomoxir, oxfenicine, perhexiline, mildronate, or ranolazine or a pharmaceutically acceptable salt of any of the preceding, within 6 hours prior to administration of a contrast agent. In embodiments, methods of preventing, reducing, and/or treating contrast-induced acute kidney injury include parenterally administering to a patient in need thereof one or more of etomoxir, oxfenicine, perhexiline, mildronate, or ranolazine or a pharmaceutically acceptable salt of any of the preceding, within 5, 4, 3, 2 or 1 hour(s) prior to administration of a contrast agent. In embodiments, methods of preventing, reducing, and/or treating contrast-induced acute kidney injury include parenterally administering to a patient in need thereof trimetazidine or pharmaceutically acceptable salt thereof, alone or in combination with one or more of etomoxir, oxfenicine, perhexiline, mildronate, or ranolazine or a pharmaceutically acceptable salt of any of the preceding, 6 hours prior to administration of a contrast agent. In embodiments, methods of preventing, reducing, and/or treating contrast-induced acute kidney injury include parenterally administering to a patient in need thereof trimetazidine or pharmaceutically acceptable salt thereof, alone or in combination with one or more of etomoxir, oxfenicine, perhexiline, mildronate, or ranolazine or a pharmaceutically acceptable salt of any of the preceding, within 5, 4, 3, 2 or 1 hour(s) prior to administration of a contrast agent. In embodiments, such parenteral administration is intravenous administration.

In embodiments, trimetazidine or pharmaceutically acceptable salt or a pharmaceutically acceptable salt thereof is administered at dosages ranging from about 0.001 mg/kg and about 10 mg/kg of body weight of a patient in need thereof, e.g., from about 0.01 mg/kg to 2.0 mg/kg at least once a day. For example, dosages may include amounts of trimetazidine or pharmaceutically acceptable salt or a pharmaceutically acceptable salt thereof in the range of about, e.g., 1 mg to 50 mg, 1 mg to 40 mg, 1 mg to 35 mg, 1 mg to 30 mg, 1 mg to 20 mg, 1 mg to 15 mg, 0.01 mg to 10 mg, 0.1 mg to 15 mg, 0.15 mg to 12.5 mg, or 0.2 mg to 10 mg, with doses of 0.1 mg, 0.2 mg, 0.3 mg, 0.4 mg, 0.5 mg, 0.6 mg, 0.7 mg, 0.8 mg, 0.9 mg, 1.5 mg, 1.0 mg, 1.75 mg, 2 mg, 2.5 mg, 2.75 mg, 3 mg, 3.5 mg, 3.75 mg, 4 mg, 4.5 mg, 4.75 mg, 5 mg, 5.5 mg, 6 mg, 6.5 mg, 7 mg, 7.5 mg, 8 mg, 8.5 mg, 9 mg, 10 mg, 11 mg, 12 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, and 200 mg being specific examples of doses.

Typically, dosages of trimetazidine or pharmaceutically acceptable salt or pharmaceutically acceptable salts thereof are administered one to four times daily to a patient in need thereof. The methods and compositions described herein may provide reduced adverse events and/or increased efficacy. In embodiments, the dosage is about, e.g., 20-100 mg/day, 20-200 mg/day or 21-100 mg/day, or 22-100 mg/day, or 23-100 mg/day, for example, 21 mg/day, 42 mg/day, 63 mg/day, 22 mg/day, 44 mg/day, 66 mg/day, 23 mg/day, 46 mg/day, 69 mg/day, 24 mg/day, 48 mg/day, 72 mg/day, 25 mg/day, 50 mg/day, 60 mg/day, 75 mg/day, 80 mg/day, 90 mg/day, 100 mg/day, 125 mg/day, 150 mg/day, 175 mg/day or 200 mg/day.

In some embodiments, provided are methods of preventing, reducing, and/or treating contrast-induced acute kidney injury by administering to a patient in need thereof 20 mg trimetazidine or a pharmaceutically acceptable salt thereof. In some embodiments the trimetazidine or pharmaceutically acceptable is provided once, twice or three times daily. In some embodiments, the trimetazidine or pharmaceutically acceptable is provided three times daily. In other embodiments, the trimetazidine or pharmaceutically acceptable is provided two times daily.

Methods of preventing, reducing, and/or treating contrast-induced acute kidney injury by administering to a subject in need thereof an effective amount of an inhibitor of fatty acid oxidation are provided. Methods of preventing, reducing, and/or treating contrast-induced acute kidney injury by administering to a subject in need thereof an effective amount of trimetazidine or pharmaceutically acceptable salt, derivative or analogue, or combination thereof, are provided. Methods of preventing, reducing, and/or treating contrast-induced acute kidney injury by administering to a subject in need thereof an effective amount of etomoxir, oxfenicine, perhexiline, mildronate, or ranolazine or a pharmaceutically acceptable salt of any of the preceding are provided. Methods of preventing, reducing, and/or treating contrast-induced acute kidney injury by administering to a subject in need thereof an effective amount of trimetazidine or pharmaceutically acceptable salt thereof in combination with an effective amount of one or more of etomoxir, oxfenicine, perhexiline, mildronate, or ranolazine or a pharmaceutically acceptable salt of any of the preceding are provided. An effective amount or therapeutically effective amount can be a dosage sufficient to treat, inhibit, or alleviate one or more symptoms of a contrast-induced acute kidney injury. In embodiments, provided are methods for the prevention of contrast-induced acute acute kidney injury (CI-AKI), in subjects with renal insufficiency undergoing diagnostic or therapeutic interventional cardiac procedures which require administration of contrast media for imaging via computed tomography (CT) or angiography.

Provided herein are dosing regimens that allow prevention and/or treatment of contrast-induced acute kidney injury with potentially limited or substantially few negative side effects, e.g., Parkinson's disease Parkinson's symptoms, or Parkinson's like symptoms. One skilled in the art may expect the use and dosage regimes provided herein to cause, or increase the risk of, Parkinsonian symptoms. Accordingly, the methods described herein may provide treatment of a contrast-induced acute kidney injury that may be considered surprising and unexpected. For example, methods are provided herein of preventing, reducing, and/or treating contrast-induced acute kidney injury in a patient in need thereof that may not cause Parkinson's like symptoms, e.g., tremors, muscle rigidity, slow movement, and impaired balance and coordination.

Trimetazidine or pharmaceutically acceptable salt thereof may be provided as an acid addition salt, a zwitter ion hydrate, zwitter ion anhydrate, dihydrochloride, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic or theophylline acetic acid addition salts, as well as the 8-halotheophyllines, for example 8-bromo-theophylline. In embodiments, inorganic acid addition salts, including but not limited to, hydrochloric, hydrobromic, sulfuric, sulfamic, phosphoric or nitric acid addition salts may be used. In embodiments, the trimetazidine may be provided as a dihydrochloride salt. One skilled in the art will readily understand that the amounts of active ingredient in a pharmaceutical composition will depend on the form of trimetazidine provided.

Deuteration of pharmaceuticals to improve pharmacokinetics (PK), pharmacodynamics (PD), and toxicity profiles, has been demonstrated previously with some classes of drugs. Accordingly the use of deuterium-enriched trimetazidine is contemplated and within the scope of the methods and compositions described herein. Deuterium can be incorporated in any position in replace of hydrogen synthetically, according to the synthetic procedures known in the art. For example, deuterium may be incorporated to various positions having an exchangeable proton, such as the amine N—H, via proton-deuterium equilibrium exchange. Thus, deuterium may be incorporated selectively or non-selectively through methods known in the art.

In embodiments, methods of treating a contrast-induced acute kidney injury include administering to a patient in need thereof a pharmaceutical composition including more than about 20 mg to about 200 mg trimetazidine or a pharmaceutically acceptable salt thereof. In embodiments, methods of treating a contrast-induced acute kidney injury include administering to a patient in need thereof a pharmaceutical composition including more than about 20 mg trimetazidine or a pharmaceutically acceptable salt thereof. In embodiments, methods of treating a contrast-induced acute kidney injury include administering to a patient in need thereof a pharmaceutical composition including more than about 35 mg trimetazidine or a pharmaceutically acceptable salt thereof.

In embodiments, the provided are methods of preventing, reducing, and/or treating contrast-induced acute kidney injury which includes administering to a patient in need thereof a first dosage regimen and a second dosage regimen of an inhibitor of fatty acid oxidation. In embodiments, the provided are methods of preventing, reducing, contrast-induced acute kidney injury which includes administering to a patient in need thereof a first dosage regimen and a second dosage regimen of trimetazidine or pharmaceutically acceptable salt thereof. In embodiments, the provided are methods of preventing, reducing, and/or treating contrast-induced acute kidney injury which includes administering to a patient in need thereof a first dosage regimen and a second dosage regimen of one or more of trimetazidine, etomoxir, oxfenicine, perhexiline, mildronate, or ranolazine or a pharmaceutically acceptable salt of any of the preceding. In embodiments, provided are methods of preventing, reducing, and/or treating contrast-induced acute kidney injury which includes administering to a patient in need thereof a first dosage regimen of trimetazidine or a pharmaceutically acceptable salt thereof and a second dosage regimen of one or more of trimetazidine, etomoxir, oxfenicine, perhexiline, mildronate, or ranolazine or a pharmaceutically acceptable salt of any of the preceding.

For example, the first dosage regimen may be a loading or initiation dosage to achieve a specific exposure of trimetazidine alone or in combination with one or more of etomoxir, oxfenicine, perhexiline, mildronate, or ranolazine in the patient.

In embodiments, trimetazidine or pharmaceutically acceptable salt thereof a may be administered multiple days before a contrast procedure, e.g., 1, 2, 3, 4, or 5 days before a contrast procedure. For example, trimetazidine or pharmaceutically acceptable salt thereof may be administered for 3 days prior to a contrast procedure. In embodiments, methods of preventing, reducing, and/or treating contrast-induced acute kidney injury include administering to a patient in need thereof trimetazidine or pharmaceutically acceptable salt thereof at least 5 days prior to a contrast procedure.

In embodiments, trimetazidine or pharmaceutically acceptable salt thereof a may be administered prior to a contrast procedure, e.g., administration to a patient 2, 3, 4, 6, 9, 10 or 12 doses of trimetazidine prior to a contrast procedure. For example, the methods may include administration of 20 mg trimetazidine or a pharamaceutically acceptable salt thereof three times daily for 3 days (e.g., 9 dosages) prior to a contrast procedure. In other examples, the methods may include administration of 20 mg trimetazidine or a pharamaceutically acceptable salt thereof three times daily for 4 days (e.g., 12 dosages) prior to a contrast procedure. In other examples, the methods may include administration of 20 mg trimetazidine or a pharamaceutically acceptable salt thereof twice daily for 3 days (e.g., 6 dosages) prior to a contrast procedure.

The loading or initiation dosage may begin prior to a contrast procedure and provide sufficient exposure to prevent contrast-induced acute injury. In embodiments, the loading dosage may be achieved by a bolus injection of trimetazidine or pharmaceutically acceptable salt thereof alone or in combination with one or more of etomoxir, oxfenicine, perhexiline, mildronate, or ranolazine or a pharmaceutically acceptable salt of any of the preceding. In embodiments, the loading dosage may be achieved by administering trimetazidine or pharmaceutically acceptable salt thereof alone or in combination with one or more of etomoxir, oxfenicine, perhexiline, mildronate, or ranolazine or a pharmaceutically acceptable salt of any of the preceding over a period of time before a contrast procedure. For example, trimetazidine or pharmaceutically acceptable salt thereof alone or in combination with one or more of etomoxir, oxfenicine, perhexiline, mildronate, or ranolazine or a pharmaceutically acceptable salt of any of the preceding, may be administered 6 hours, 12, or 24 hours prior to a contrast procedure. In embodiments, trimetazidine or pharmaceutically acceptable salt thereof alone or in combination with one or more of etomoxir, oxfenicine, perhexiline, mildronate, or ranolazine or a pharmaceutically acceptable salt of any of the preceding, may be parenterally administered 6 hours, 12, or 24 hours prior to a contrast procedure. In embodiments, trimetazidine or pharmaceutically acceptable salt thereof alone or in combination with one or more of etomoxir, oxfenicine, perhexiline, mildronate, or ranolazine or a pharmaceutically acceptable salt of any of the preceding, may be intravenously administered 6 hours, 12, or 24 hours prior to a contrast procedure. In embodiments, trimetazidine or pharmaceutically acceptable salt thereof, alone or in combination with one or more of etomoxir, oxfenicine, perhexiline, mildronate, or ranolazine or a pharmaceutically acceptable salt of any of the preceding, may be administered within 6 hours prior to administration of a contrast agent. In embodiments, trimetazidine or pharmaceutically acceptable salt thereof alone or in combination with one or more of etomoxir, oxfenicine, perhexiline, mildronate, or ranolazine or a pharmaceutically acceptable salt of any of the preceding, may be administered within 5 hours prior to administration of a contrast agent. In embodiments, trimetazidine or pharmaceutically acceptable salt thereof, alone or in combination with one or more of etomoxir, oxfenicine, perhexiline, mildronate, or ranolazine or a pharmaceutically acceptable salt of any of the preceding, may be administered within 4 hours prior to administration of a contrast agent. In embodiments, trimetazidine or pharmaceutically acceptable salt thereof alone or in combination with one or more of etomoxir, oxfenicine, perhexiline, mildronate, or ranolazine or a pharmaceutically acceptable salt of any of the preceding, may be administered within 3 hours prior to administration of a contrast agent. In embodiments, trimetazidine or pharmaceutically acceptable salt thereof, alone or in combination with one or more of etomoxir, oxfenicine, perhexiline, mildronate, or ranolazine or a pharmaceutically acceptable salt of any of the preceding, may be administered within 2 hours prior to administration of a contrast agent. In embodiments, trimetazidine or pharmaceutically acceptable salt thereof alone or in combination with one or more of etomoxir, oxfenicine, perhexiline, mildronate, or ranolazine or a pharmaceutically acceptable salt of any of the preceding, may be administered within 1 hour prior to administration of a contrast agent. In embodiments, trimetazidine or pharmaceutically acceptable salt thereof alone or in combination with one or more of etomoxir, oxfenicine, perhexiline, mildronate, or ranolazine or a pharmaceutically acceptable salt of any of the preceding, may be administered parenterally when being administered within 6 hours or less, e.g., less than 5.75 hours, 5.5 hours, 5.25 hours, 5 hours, 4.75 hours, 4.5 hours, 4.25 hours, 3 hours, 2.75 hours, 2.5 hours, 2.25 hours, 2 hours, 1.75 hours, 1.5 hours, 1.25 hours, 1 hour, 0.75 hour, 0.5 hour, or 0.25 hour. In embodiments, one or more of trimetazidine, etomoxir, oxfenicine, perhexiline, mildronate, or ranolazine or a pharmaceutically acceptable salt of any of the preceding, may be administered parenterally when being administered within 6 hours or less, e.g., less than 5.75 hours, 5.5 hours, 5.25 hours, 5 hours, 4.75 hours, 4.5 hours, 4.25 hours, 3 hours, 2.75 hours, 2.5 hours, 2.25 hours, 2 hours, 1.75 hours, 1.5 hours, 1.25 hours, 1 hour, 0.75 hour, 0.5 hour, or 0.25 hour. In embodiments, trimetazidine or pharmaceutically acceptable salt thereof alone or in combination with one or more of etomoxir, oxfenicine, perhexiline, mildronate, or ranolazine or a pharmaceutically acceptable salt of any of the preceding, may be administered intravenously when being administered within 6 hours or less, e.g., less than 5.75 hours, 5.5 hours, 5.25 hours, 5 hours, 4.75 hours, 4.5 hours, 4.25 hours, 3 hours, 2.75 hours, 2.5 hours, 2.25 hours, 2 hours, 1.75 hours, 1.5 hours, 1.25 hours, 1 hour, 0.75 hour, 0.5 hour, or 0.25 hour. In embodiments, one or more of trimetazidine, etomoxir, oxfenicine, perhexiline, mildronate, or ranolazine or a pharmaceutically acceptable salt of any of the preceding, may be administered intravenously when being administered within 6 hours or less, e.g., less than 5.75 hours, 5.5 hours, 5.25 hours, 5 hours, 4.75 hours, 4.5 hours, 4.25 hours, 3 hours, 2.75 hours, 2.5 hours, 2.25 hours, 2 hours, 1.75 hours, 1.5 hours, 1.25 hours, 1 hour, 0.75 hour, 0.5 hour, or 0.25 hour. In embodiments, trimetazidine or pharmaceutically acceptable salt thereof alone or in combination with one or more of etomoxir, oxfenicine, perhexiline, mildronate, or ranolazine or a pharmaceutically acceptable salt of any of the preceding, may be administered intravenously regardless of the time of administration. In embodiments, trimetazidine or pharmaceutically acceptable salt thereof etomoxir, oxfenicine, perhexiline, mildronate or ranolazine may be administered multiple days prior to a contrast procedure, e.g., one, two, three, four, five, six, etc. days prior to a contrast procedure. In embodiments, the loading or initiation dosage regime will be administered three days prior to a contrast procedure.

The second dosage regimen may be a continuation dosage to achieve and/or maintain a specific exposure of trimetazidine, etomoxir, oxfenicine. perhexiline, mildronate, or ranolazine in the patient. The continuation dosage may begin just after a contrast procedure and provide sufficient exposure to prevent contrast-induced acute injury. The continuation dosage may be achieved by administering trimetazidine or pharmaceutically acceptable salt thereof alone or in combination with one or more of etomoxir, oxfenicine, perhexiline, mildronate, or ranolazine, or a pharmaceutically acceptable salt of any of the preceding over a period of time after a contrast procedure. For example, trimetazidine or pharmaceutically acceptable salt thereof alone or in combination with one or more of etomoxir, oxfenicine, perhexiline, mildronate, or ranolazine, or a pharmaceutically acceptable salt of any of the preceding may be administered 6 hours, 12, or 24 hours after a contrast procedure. In embodiments, trimetazidine or pharmaceutically acceptable salt thereof alone or in combination with one or more of etomoxir, oxfenicine, perhexiline, mildronate. or ranolazine, or a pharmaceutically acceptable salt of any of the preceding may be administered multiple days after a contrast procedure, e.g., one, two, three, four, five, six, etc. days after a contrast procedure. In embodiments, the continuation dosage regime will be administered for a period of weeks, e.g., 6, 8, 10 or 12 weeks, after a contrast procedure. In some examples, the continuation dosage will be administered for a period of about 90 days. In specific examples, the continuation dosage will be administered for a period of about 87 days. For example, in embodiments, the initiation dosage will be administered for 3 days prior to a contrast procedure and the continuation dosage may be administered for a period of 87 days. Accordingly in some examples, the methods disclosed contemplate the administration of the dosages and profiles described herein for a period of 90 days.

In embodiments, trimetazidine or pharmaceutically acceptable salt thereof a may be administered multiple days after a contrast procedure, e.g., 5, 10, 15, 20, 25, 30, 35, 40, 45, 50, 60, 65, 70, 75, 80, 85 90, 95, or 100 days after a contrast procedure. For example, trimetazidine or pharmaceutically acceptable salt thereof a may be administered for 90 days after a contrast procedure. In embodiments, methods of preventing, reducing, and/or treating contrast-induced acute kidney injury include administering to a patient in need thereof trimetazidine or pharmaceutically acceptable salt thereof for at least 90 days.

In embodiments, the first dosage regimen and second dosage regimen may be the same or a different dosage of trimetazidine or pharmaceutically acceptable salt thereof alone or in combination with one or more of etomoxir, oxfenicine, perhexiline, mildronate, or ranolazine, or a pharmaceutically acceptable salt of any of the preceding. Thus, the first dosage regimen and second dosage regimen may provide the same or a different profile of trimetazidine, etomoxir, oxfenicine, perhexiline, mildronate, or ranolazine in the patient (e.g., $C_{max}$, $AUC_{0-\infty}$) as described herein. In embodiments, the first dosage regimen and second dosage regimen provide the same exposure of trimetazidine, etomoxir, oxfenicine, perhexiline, mildronate, or ranolazine.

In embodiments, the methods and pharmaceutical compositions include 21 mg to 25 mg, 21 mg to 23 mg, 21 mg to 35 mg, 20.5 mg to 25 mg, 22 mg to 30 mg, 20 to 45 mg, 21 mg to 75 mg, 21 mg to 50 mg, 21 mg to 45 mg, 22 mg to 75 mg, 22 mg to 50 mg, 22 mg to 45 mg, 22 mg to 35 mg, 21 mg to 30 mg, 23 mg to 75 mg, 23 mg to 55 mg, 23 mg to 40 mg, 23 mg to 55 mg, 24 mg to 35 mg, 24 mg to 50 mg, 24 mg to 35 mg trimetazidine or a pharmaceutically acceptable salt thereof.

In embodiments, the methods and pharmaceutical compositions include 20 mg to 30 mg, 21 mg to 30 mg, 22 mg to 30 mg, 23 mg to 30 mg, 24 mg to 25 mg, 21 mg to 50 mg, 21 mg to 24 mg, 21 mg to 23 mg, or 21 mg to 22 mg trimetazidine or a pharmaceutically acceptable salt thereof.

In embodiments, the methods and pharmaceutical compositions include, e.g., 20.1 mg, 20.25 mg, 20.5 mg, 21 mg, 21.5 mg, 23 mg, 24 mg, 25 mg, 22 mg, 22.5 mg, 23 mg, 23.5 mg, 24 mg, 24.5 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 34 mg, 34.5 mg or 35 mg trimetazidine or a pharmaceutically acceptable salt thereof or amounts that are multiples of such doses. In embodiments, the pharmaceutical compositions include 21 mg, 22 mg, 23 mg, 24 mg, 25 mg, or 26 mg trimetazidine or a pharmaceutically acceptable salt thereof.

Pharmaceutical compositions herein may be provided with immediate release, delayed release, extended release, or modified release profiles. In addition, compositions herein may be provided for parenteral administration (e.g., intramuscular, intravenous, subcutaneous, intraperitoneal, or intrathecal). In embodiments, pharmaceutical compositions may be provided with immediate release profile. In embodiments, pharmaceutical compositions with different drug release profiles may be combined to create a two phase or three-phase release profile. For example, pharmaceutical compositions may be provided with an immediate release and an extended release profile. In embodiments, pharmaceutical compositions may be provided with an extended release and delayed release profile. Such composition may be provided as pulsatile formulations, multilayer tablets, or capsules containing tablets, beads, granules, etc. Compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions.

Parenteral compositions must be sterile for administration by injection, infusion or implantation into the body and may be packaged in either single-dose or multi-dose containers. In embodiments, liquid pharmaceutical compositions for parenteral administration to a subject include an active substance, e.g., an inhibitor of fatty acid oxidation. In embodiments, liquid pharmaceutical compositions for parenteral administration to a subject include an active substance, e.g., trimetazidine or pharmaceutically acceptable salt thereof alone or in combination with one or more of etomoxir, oxfenicine, perhexiline, mildronate, or ranolazine, or a pharmaceutically acceptable salt of any of the preceding, in any of the respective amounts described herein. In embodiments, the pharmaceutical compositions for parenteral administration are formulated as a total volume of about, e.g., 10 ml, 20 ml, 25 ml, 50 ml, 100 ml, 200 ml, 250 ml, or 500 ml. In embodiments, the compositions are contained in a bag, a glass vial, a plastic vial, or a bottle.

In embodiments, pharmaceutical compositions for parenteral administration include about 0.05 mg to about 100 mg active substance, e.g., an inhibitor of fatty acid oxidation. In embodiments, pharmaceutical compositions for parenteral administration include about 0.05 mg to about 100 mg active substance, e.g., trimetazidine or pharmaceutically acceptable salt thereof alone or in combination with one or more of etomoxir, oxfenicine, perhexiline, mildronate, or ranolazine, or a pharmaceutically acceptable salt of any of the preceding. In embodiments, the pharmaceutical compositions for parenteral administration include about, e.g., 0.1 mg to 50 mg, 0.1 mg to 40 mg, 0.1 mg to 35 mg, 0.5 mg to 25 mg, 0.5 mg to 20 mg, 0.5 to 15 mg, 0.5 to 35 mg, 1 mg to 35 mg, 1 mg to 30 mg, 1 mg to 25 mg, 1 mg to 20 mg, 1 mg to 15 mg, 1.5 mg to 35 mg, 1.5 mg to 30 mg, 1.5 mg to 25 mg, 1.5 mg to 20 mg, 1.5 mg to 15 mg, 2 mg to 35 mg, 2 mg to 30 mg, 2 mg to 25 mg, 2 mg to 20 mg, 2 mg to 15 mg, 2.5 mg to 35 mg, 2.5 mg to 30 mg, 2.5 mg to 25 mg, 2.5 mg to 20 mg, 2.5 mg to 15 mg, 3 mg to 35 mg, 3 mg to 30 mg, 3 mg to 25 mg, 3 mg to 20 mg, 3 mg to 15 mg active substance, e.g., trimetazidine or pharmaceutically acceptable salt thereof alone or in combination with one or more of etomoxir, oxfenicine, perhexiline, mildronate, or ranolazine, or a pharmaceutically acceptable salt of any of the preceding.

In embodiments, pharmaceutical compositions for parenteral administration to a subject include an active substance, e.g., trimetazidine or pharmaceutically acceptable salt thereof alone or in combination with one or more of etomoxir, oxfenicine, perhexiline, mildronate, or ranolazine, or a pharmaceutically acceptable salt of any of the preceding, at a respective concentration of about 0.005 mg/ml to about 500 mg/ml. In embodiments, the pharmaceutical composition for parenteral administration includes an active substance, e.g., trimetazidine or pharmaceutically acceptable salt thereof alone or in combination with one or more of etomoxir, oxfenicine, perhexiline, mildronate, or ranolazine, or a pharmaceutically acceptable salt of any of the preceding, at a respective concentration of, e.g., about 0.05 mg/ml to about 50 mg/ml, about 0.1 mg/ml to about 50 mg/ml, about 0.1 mg/ml to about 10 mg/ml, about 0.05 mg/ml to about 25 mg/ml, about 0.05 mg/ml to about 10 mg/ml, about 0.05 mg/ml to about 5 mg/ml, or about 0.05 mg/ml to about 1 mg/ml. In embodiments, the pharmaceutical composition for parenteral administration includes an active substance, e.g., trimetazidine or pharmaceutically acceptable salt thereof alone or in combination with one or more of etomoxir, oxfenicine, perhexiline, mildronate, or ranolazine, or a pharmaceutically acceptable salt of any of the preceding, at a respective concentration of, e.g., about 0.05 mg/ml to about 15 mg/ml, about 0.5 mg/ml to about 10 mg/ml, about 0.25 mg/ml to about 5 mg/ml, about 0.5 mg/ml to about 7 mg/ml, about 1 mg/ml to about 10 mg/ml, about 5 mg/ml to about 10 mg/ml, or about 5 mg/ml to about 15 mg/ml. In embodiments, pharmaceutical compositions for parenteral administration are formulated as a total volume of about, e.g., 10 ml, 20 ml, 25 ml, 50 ml, 100 ml, 200 ml, 250 ml, or 500 ml. In embodiments, the compositions are packages and stored in a bag, a glass vial, a plastic vial, or a bottle.

In embodiments, the solubility of the active substance, e.g., an inhibitor of fatty acid oxidation, in the pharmaceutical composition for parenteral administration may be greater than, e.g., about 10 mg/mL, about 15 mg/mL, about 20 mg/mL, about 25 mg/mL, about 30 mg/mL, about 40 mg/mL, about 50 mg/mL, about 75 mg/mL, about 100 mg/mL, about 150 mg/mL, when measured, for example, in water at 25° C. In embodiments, the solubility of the active substance, e.g., trimetazidine or pharmaceutically acceptable salt thereof alone or in combination with one or more of etomoxir, oxfenicine, perhexiline, mildronate, or ranolazine, or a pharmaceutically acceptable salt of any of the preceding, in the pharmaceutical composition for parenteral administration may be greater than, e.g., about 10 mg/mL, about 15 mg/mL, about 20 mg/mL, about 25 mg/mL, about 30 mg/mL, about 40 mg/mL, about 50 mg/mL, about 75 mg/mL, about 100 mg/mL, about 150 mg/mL, when measured, for example, in water at 25° C. In embodiments, the solubility of the active substance, e.g., an inhibitor of fatty acid oxidation in the composition may be between, e.g., about 1 mg/mL to about 50 mg/mL, about 5 mg/mL to about 50 mg/mL, about 10 mg/mL to about 50 mg/mL, about 20 mg/mL to about 50 mg/ml, from about 20 mg/mL to about 30 mg/mL or from about 10 mg/mL to about 45 mg/mL, when measured, for example, in water at 25 C.

In embodiments, the solubility of the active substance, e.g., trimetazidine or pharmaceutically acceptable salt thereof alone or in combination with one or more of etomoxir, oxfenicine, perhexiline, mildronate, or ranolazine, or a pharmaceutically acceptable salt of any of the preceding, in the composition may be between, e.g., about 1 mg/mL to about 50 mg/mL, about 5 mg/mL to about 50 mg/mL, about 10 mg/mL to about 50 mg/mL, about 20 mg/mL to about 50 mg/ml, from about 20 mg/mL to about 30 mg/mL or from about 10 mg/mL to about 45 mg/mL, when measured, for example, in water at 25 C.

In embodiments, a pharmaceutical composition for parenteral administration is provided wherein the pharmaceutical composition is stable for at least six months. In embodiments, the pharmaceutical compositions for parenteral administration exhibit no more than about 5% decrease in active substance, e.g., trimetazidine or pharmaceutically acceptable salt thereof alone or in combination with one or more of etomoxir, oxfenicine, perhexiline, mildronate, or ranolazine, or a pharmaceutically acceptable salt of any of the preceding, e.g., 3 months or 6 months. In embodiments, the amount of trimetazidine or pharmaceutically acceptable salt thereof alone or in combination with one or more of etomoxir, oxfenicine, perhexiline, mildronate, or ranolazine, or a pharmaceutically acceptable salt of any of the preceding, degrades at no more than about, e.g., 2.5%, 1%, 0.5% or 0.1%. In embodiments, the degradation is less than about, e.g., 5%, 2.5%, 1%, 0.5%, 0.25%, 0.1%, for at least six months.

In embodiments, pharmaceutical compositions for parenteral administration are provided wherein the pharmaceutical composition remains soluble. In embodiments, pharmaceutical compositions for parenteral administration are provided that are stable, soluble, local site compatible and/or ready-to-use. In embodiments, the pharmaceutical compositions herein are ready-to-use for direct administration to a patient in need thereof.

The parenteral compositions provided herein may include one or more excipients, e.g., solvents, solubility enhancers, suspending agents, buffering agents, isotonicity agents, stabilizers or antimicrobial preservatives. When used, the excipients of the parenteral compositions will not adversely affect the stability, bioavailability, safety, and/or efficacy of trimetazidine or pharmaceutically acceptable salt thereof alone or in combination with one or more of etomoxir, oxfenicine, perhexiline, mildronate, or ranolazine, or a pharmaceutically acceptable salt of any of the preceding used in the composition. Thus, parenteral compositions are provided wherein there is no incompatibility between any of the components of the dosage form.

In embodiments, parenteral compositions including trimetazidine or pharmaceutically acceptable salt thereof alone or in combination with one or more of etomoxir, oxfenicine, perhexiline, mildronate, or ranolazine, or a pharmaceutically acceptable salt of any of the preceding include a stabilizing amount of at least one excipient. For example, excipients may be include buffering agents, solubilizing agents, tonicity agents, antioxidants, chelating agents, antimicrobial agents, and preservatives. One skilled in the art will appreciate that an excipient may have more than one function and be classified in one or more defined group.

In embodiments, parenteral compositions including trimetazidine or pharmaceutically acceptable salt thereof alone or in combination with one or more of etomoxir, oxfenicine, perhexiline, mildronate, or ranolazine, or a pharmaceutically acceptable salt of any of the preceding, and an excipient wherein the excipient is present at a weight percent (w/v) of less than about, e.g., 10%, 5%, 2.5%, 1%, or 0.5%. In embodiments, the excipient is present at a weight percent between about, e.g., 1.0% to 10%, 10% to 25%, 15% to 35%, 0.5% to 5%, 0.001% to 1%, 0.01% to 1%, 0.1% to 1%, or 0.5% to 1%. In embodiments, the excipient is present at a weight percent between about, e.g., 0.001% to 1%, 0.01% to 1%, 1.0% to 5%, 10% to 15%, or 1% to 15%.

In embodiments, parenteral compositions may be administered as needed, e.g., once, twice, thrice or four or more times daily, or continuously depending on the patient's needs.

In embodiments, parenteral compositions of an active substance, e.g., trimetazidine or pharmaceutically acceptable salt thereof alone or in combination with one or more of etomoxir, oxfenicine, perhexiline, mildronate, or ranolazine, or a pharmaceutically acceptable salt of any of the preceding are provided, wherein the pH of the composition is between about 4.0 to about 8.0. In embodiments, the pH of the compositions is between, e.g., about 5.0 to about 8.0, about 6.0 to about 8.0, about 6.5 to about 8.0. In embodiments, the pH of the compositions is between, e.g., about 6.5 to about 7.5, about 7.0 to about 7.8, about 7.2 to about 7.8, or about 7.3 to about 7.6. In embodiments, the pH of the aqueous solution is, e.g., about 6.8, about 7.0, about 7.2, about 7.4, about 7.6, about 7.7, about 7.8, about 8.0, about 8.2, about 8.4, or about 8.6.

In embodiments, the methods and pharmaceutical compositions described herein are administered once, twice, three or four times daily, or every other day. In embodiments, a pharmaceutical composition described herein is provided to the patient in the evening. In embodiments, a pharmaceutical composition described herein is provided to the patient once in the evening and once in the morning.

In embodiments, the total amount of trimetazidine or pharmaceutically acceptable salt thereof administered to a subject in a 24-hour period is 20 mg to 200 mg. In embodiments, the total amount of trimetazidine or pharmaceutically acceptable salt thereof administered to a subject in a 24-hour period is 20 mg to 100 mg. In embodiments, the total amount of trimetazidine or pharmaceutically acceptable salt thereof administered to a subject in a 24-hour period is 20 mg to 80 mg. In embodiments, the total amount of trimetazidine or pharmaceutically acceptable salt thereof administered to a subject in a 24-hour period is more than about 20 mg, 40 mg, or 60 mg. In embodiments, the total amount of trimetazidine or a pharmaceutically acceptable salt thereof administered to a subject in a 24-hour period is more than about 20 mg to 60 mg.

In embodiments, provided herein are methods of preventing, reducing, and/or treating contrast-induced acute kidney injury by administering to a patient in need thereof an effective amount of trimetazidine or pharmaceutically acceptable salt thereof alone or in combination with one or more of etomoxir, oxfenicine, perhexiline, mildronate, or ranolazine, or a pharmaceutically acceptable salt of any of the preceding. An effective amount or therapeutically effective amount can be a dosage sufficient to treat, inhibit, or alleviate one or more symptoms of a contrast-induced acute kidney injury. For example, an effective amount of trimetazidine may be established by measuring the proportion of patients developing a relative decrease of >=30% in estimated or measured glomerular filtration rate (GFR) after some amount of time (e.g., 15, 30, 60 or 90 days) following the administration of a contrast agent. In other examples, an effective amount of trimetazidine, etomoxir, oxfenicine, perhexiline, mildronate, or ranolazine may be established by measuring the proportion of patients with reduction in or loss of kidney function following the administration of a contrast agent. In embodiments, the methods include administering trimetazidine or a pharmaceutically acceptable salt thereof to a patient with an estimated glomerular filtration rate, e.g., below 90 mL/min/1.73 m$^2$, between about 15-90 mL/min/1.73 m$^2$, between about 60-90 mL/min/1.73 m$^2$, or between about 15-60 mL/min/1.73 m$^2$.

In embodiments, a reduction or loss of kidney function may be determined by measuring an absolute increase of >=0.3 mg/dL in serum creatinine concentration between baseline and at any time (e.g., up to seven days) following the administration of a contrast agent. In embodiments, the methods include administering trimetazidine or a pharmaceutically acceptable salt thereof to a patient with an creatinine level of 0.4 to 1.3 milligrams (mg) per deciliter (dL).

In embodiments, the methods include administering trimetazidine or a pharmaceutically acceptable salt thereof to a patient with an creatinine level of less than 1.5 milligrams (mg) per deciliter (dL). In embodiments, the methods include administering trimetazidine or a pharmaceutically acceptable salt thereof to a patient with an creatinine level of 1.5 to 2.0 milligrams (mg) per deciliter (dL). In embodiments, the methods include administering trimetazidine or a pharmaceutically acceptable salt thereof to a patient with an creatinine level of 2.0 to 5.0 milligrams (mg) per deciliter (dL). In embodiments, the methods include administering trimetazidine or a pharmaceutically acceptable salt thereof to a patient with an creatinine level of 5.0 to 8.0 milligrams (mg) per deciliter (dL). In embodiments, the methods include administering trimetazidine or a pharmaceutically acceptable salt thereof to a patient with an creatinine level of higher than 8.0 milligrams (mg) per deciliter (dL).

In embodiments, a reduction or loss of kidney function may be determined by measuring a relative increase of >=50% in serum creatinine concentration between baseline and at any time (e.g., up to seven days) following the administration of a contrast agent. In embodiments, a reduction or loss of kidney function may be determined by measuring a relative decrease of >=30% in estimated or measured glomerular filtration rate (GFR) between baseline and at any time up (e.g., up to seven days) following the administration of a contrast agent.

In embodiments, provided herein are methods of preventing, reducing, and/or treating contrast-induced acute kidney injury by administering to a patient in need thereof an effective amount of an inhibitor of fatty acid oxidation before, during and after procedures involving use of devices such as guide wires and intracoronary pressure wires, cardiac catheters such as balloon catheters, atherectomy devices such as rotational atherectomy catheters, intracoronary stents including bare metal stents, drug- (such as sirolimus, paclitaxel, everolimus and zotarolimus) eluting stents, stents coated with bioabsorbable polymers and stents with fully bioresorbable scaffolds, thrombus extraction catheters, embolic protection devices, replacement cardiac valves and/or vascular closure devices. In embodiments, provided herein are methods of preventing, reducing, and/or treating contrast-induced acute kidney injury by administering to a patient in need thereof an effective amount of trimetazidine or pharmaceutically acceptable salt thereof alone or in combination with one or more of etomoxir, oxfenicinc, perhexiline, mildronate, or ranolazine, or a pharmaceutically acceptable salt of any of the preceding, before, during and after procedures involving use of devices such as guide wires and intracoronary pressure wires, cardiac catheters such as balloon catheters, atherectomy devices such as rotational atherectomy catheters, intracoronary stents including bare metal stents, drug- (such as sirolimus, paclitaxel, everolimus and zotarolimus) eluting stents, stents coated with bioabsorbable polymers and stents with fully bioresorbable scaffolds, thrombus extraction catheters, embolic protection devices, replacement cardiac valves and/or vascular closure devices.

In embodiments, provided herein are methods of preventing, reducing, and/or treating contrast-induced acute kidney injury by administering to a patient in need thereof an effective amount of trimetazidine or pharmaceutically acceptable salt thereof in combination with or before and after administration of contrast media such as barium sulfate, iodine, and gadolinium, anticoagulants such as acetylsalicylic acid, unfractionated heparin, low-molecular weight heparin (enoxaparin), synthetic pentasaccharides/Factor Xa inhibitors (including fondaparinux), dipyridamole, argatroban, and/or bivalirudin, ticlopidine, cilostazol, and antiplatelet agents such as cangrelor, clopidogrel, prasugrel, ticagrelor, aspirin, and/or glycoprotein IIb/IIIa antagonists such as abciximab, eptifibatide and tirofiban.

In embodiments, provided herein are methods of preventing, reducing, and/or treating contrast-induced acute kidney injury which include administering to a patient in need thereof trimetazidine or a pharmaceutically acceptable salt thereof wherein the composition provides an in vivo plasma profile having a $C_{max}$ more than about 65 µg/ml.

In embodiments, the composition provides an in vivo plasma profile having a $C_{max}$ more than about, e.g., 75 µg/ml, 85 ng/ml, 90 ng/ml, or 100 ng/ml. In embodiments, the composition provides an in vivo plasma profile having a $C_{max}$ less than about, e.g., 250 µg/ml, 200 µg/ml 150 µg/ml, or 100 µg/ml. In embodiments, provided herein are methods of treating a contrast-induced acute kidney injury including administering to a patient in need thereof a pharmaceutical composition including an active substance, e.g., trimetazidine or pharmaceutically acceptable salt, wherein the composition provides an in vivo plasma profile having a $C_{max}$ more than about 100 µg/ml.

The effective amount of an inhibitor of fatty acid oxidation necessary for administration may depend on a number of factors. The effective amount of trimetazidine or pharmaceutically acceptable salt necessary for administration may depend on a number of factors. The effective amount of etomoxir, oxfenicine, perhexiline, mildronate, or ranolazine, or a pharmaceutically acceptable salt of any of the preceding necessary for administration may depend on a number of factors. For example, a dosage sufficient to treat, inhibit, or alleviate one or more symptoms of a contrast-induced acute kidney injury will depend on the actual exposure (AUC) experienced by the patient. Accordingly, in some examples, subjects with renal insufficiency undergoing diagnostic or interventional cardiac procedures that require administration of contrast media may require less inhibitor of fatty acid oxidation to reach an exposure that provides an effective amount. In some examples, subjects with renal insufficiency undergoing diagnostic or interventional cardiac procedures that require administration of contrast media may require less trimetazidine or pharmaceutically acceptable salt thereof to reach an exposure that provides an effective amount. In some examples, subjects with renal insufficiency undergoing diagnostic or interventional cardiac procedures that require administration of contrast media may require less etomoxir, oxfenicine, perhexiline, mildronate, or ranolazine, or a pharmaceutically acceptable salt of any of the preceding to reach an exposure that provides an effective amount.

In embodiments, provided herein are methods of preventing, reducing, and/or treating contrast-induced acute kidney injury which includes administering to a patient in need thereof trimetazidine or a pharmaceutically acceptable salt thereof wherein the composition provides an in vivo plasma profile having an AUC more than about 500 µg hr/ml.

In embodiments, provided herein are methods of preventing, reducing, and/or treating a contrast-induced acute kidney injury including administering to a patient in need thereof a pharmaceutical composition wherein the composition provides a consistent in vivo plasma profile having a $AUC_{0-\infty}$ of more than about 500 µg·hr/ml In embodiments, the compositions provide an in vivo plasma profile having a $AUC_{0-\infty}$ of more than about, e.g., 550 µg·hr/ml, 600 µg·hr/ml, 650 µg·hr/ml, 850 µg·hr/ml, 800 µg·hr/ml, 750 µg·hr/ml, or 700 µg·hr/ml, 900 µg·hr/ml, 1000 µg·hr/ml, 1250 µg·hr/ml, 1500 µg·hr/ml. 2000 µg·hr/ml, 3000 µg·hr/ml, 4000 µg·hr/ml, or 5000 µg·hr/ml.

In embodiments, the patient in need thereof is administered trimetazidine or a pharmaceutically acceptable salt thereof to maintain a $AUC_{0-\infty}$ more than 48 hours prior to undergoing a cardiac procedure. For example, the methods may provide and maintain an in vivo plasma profile having a $AUC_{0-\infty}$ of more than about, e.g., 500 µg·hr/ml, 600 µg·hr/ml, 750 µg·hr/ml, or 1000 µg·hr/ml.

In embodiments, the patient in need thereof is administered trimetazidine or a pharmaceutically acceptable salt thereof to maintain a $AUC_{0-\infty}$ for more than 30 days after undergoing a cardiac procedure. In embodiments, the patient in need thereof is administered trimetazidine or a pharmaceutically acceptable salt thereof to maintain a $AUC_{0-\infty}$ for more than 60 days after undergoing a cardiac procedure. In embodiments, the patient in need thereof is administered trimetazidine or a pharmaceutically acceptable salt thereof to maintain a $AUC_{0-\infty}$ for more than 75 days after undergoing a cardiac procedure. In embodiments, the patient in need thereof is administered trimetazidine or a pharmaceutically acceptable salt thereof to maintain a $AUC_{0-\infty}$ for more than 90 days after undergoing a cardiac procedure. For example, the methods may provide and maintain an in vivo plasma profile having a $AUC_{0-\infty}$ of more than about, e.g., 500 µg·hr/ml, 600 µg·hr/ml, 750 µg·hr/ml, or 1000 µg·hr/ml. In embodiments, the patient in need thereof is administered trimetazidine or a pharmaceutically acceptable salt thereof to maintain a $AUC_{0-\infty}$ for a total of 90 days.

In embodiments, methods of preventing, reducing and/or treating contrast-induced acute kidney injury including administering to a patient in need thereof trimetazidine or a pharmaceutically acceptable salt thereof in an amount of more than 20 mg. The patient may undergoing a cardiac procedure that requires administration of contrast media for imaging. In some embodiments, the patient may be administered trimetazidine or a pharmaceutically acceptable salt thereof prior to undergoing a cardiac procedure. For example, the patient may be administered trimetazidine or a pharmaceutically acceptable salt thereof for more than 48 hours prior to undergoing a cardiac procedure. In some examples, the patient in need thereof may be administered trimetazidine or a pharmaceutically acceptable salt thereof for at least 96 hours prior to undergoing a cardiac procedure (e.g., receiving contrast agent). The trimetazidine or pharmaceutically acceptable salt thereof may be administered twice daily. In some embodiments, the trimetazidine or pharmaceutically acceptable salt thereof may be administered three times daily. In some embodiments, the patient in need thereof is administered trimetazidine or a pharmaceutically acceptable salt thereof three times daily for 48 hours prior to undergoing a cardiac procedure (e.g., receiving contrast agent). In some embodiments, the patient is administered trimetazidine or a pharmaceutically acceptable salt thereof for more than 60 days after undergoing a cardiac procedure. In some embodiments, the patient in need thereof is administered trimetazidine or a pharmaceutically acceptable salt thereof three times daily for 90 days after administration of a contrast agent. For example, the total amount of trimetazidine or a pharmaceutically acceptable salt thereof administered to the patient in a 24-hour period may be about 60 mg.

In some embodiments, trimetazidine or a pharmaceutically acceptable salt thereof is administered to the patient before, during and/or after a surgical procedure involving use of one or more of a guide wire, intracoronary pressure wire, cardiac catheter, atherectomy device, intracoronary stent, thrombus extraction catheter, embolic protection device, replacement cardiac valve or vascular closure device. In some embodiments, trimetazidine or a pharmaceutically acceptable salt thereof is administered to the patient before, during and/or after a cardiac procedure that includes a contrast medium, an anticoagulant and/or an anti-platelet agent. In some embodiments, trimetazidine or a pharmaceutically acceptable salt thereof is administered in combination with one or more of etomoxir, oxfenicine, perhexiline, mildronate, or ranolazine, or a pharmaceutically acceptable salt of any of the preceding.

In some embodiments, methods of preventing and/or treating contrast-induced acute kidney injury include administering to a patient in need thereof trimetazidine or a pharmaceutically acceptable salt thereof wherein the composition provides an in vivo plasma profile defining a $C_{max}$ more than about 65 µg/ml. In some embodiments, methods of preventing and/or treating contrast-induced acute kidney injury include administering to a patient in need thereof trimetazidine or a pharmaceutically acceptable salt thereof wherein the composition provides an in vivo plasma profile defining an AUC more than about 500 µg hr/ml. For example, the patient may be undergoing a cardiac procedure that requires administration of contrast media for imaging. In some embodiments, the patient is administered trimetazidine or a pharmaceutically acceptable salt thereof for 48 hours prior to undergoing a cardiac procedure (e.g., receiving contrast media). In some examples, the patient in need thereof may be administered trimetazidine or a pharmaceutically acceptable salt thereof for at least 96 hours prior to undergoing a cardiac procedure (e.g., receiving contrast agent). The trimetazidine or pharmaceutically acceptable salt thereof may be administered twice daily. In some embodiments, the trimetazidine or pharmaceutically acceptable salt thereof may be administered three times daily. In some embodiments, the patient in need thereof is administered trimetazidine or a pharmaceutically acceptable salt thereof three times daily for 48 hours prior to undergoing a cardiac procedure (e.g., receiving contrast agent). In some embodiments, the patient is administered trimetazidine or a pharmaceutically acceptable salt thereof for more than 60 days after undergoing a cardiac procedure. In some embodiments, the patient in need thereof is administered trimetazidine or a pharmaceutically acceptable salt thereof three times daily for 90 days after administration of a contrast agent. For example, the total amount of trimetazidine or a pharmaceutically acceptable salt thereof administered to the patient in a 24-hour period may be about 60 mg.

In embodiments, methods of treating and/or preventing contrast-induced acute kidney injury include administration of trimetazidine or pharmaceutically acceptable salt, pharmaceutically acceptable salts, derivatives and/or analogues thereof in combination with one or more other active agents. The combination therapies can include administration of the active agent together in the same admixture, or in separate admixtures. In embodiments, the pharmaceutical composition includes two, three, or more active agents.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "treating" or "treatment" refers to alleviating, attenuating or delaying the appearance of clinical symptoms of a disease or condition in a subject that may be afflicted with or predisposed to the disease or condition, but does not yet experience or display clinical or subclinical symptoms of the disease or condition. In embodiments, treating" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating" or "treatment" may also refer to inhibiting the disease or condition, e.g., arresting or reducing at least one clinical or subclinical symptom thereof. "Treating" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic treatment are two separate embodiments of the disclosure herein.

"Effective amount" or "therapeutically effective amount" means a dosage sufficient to alleviate one or more symptom of a disorder, disease, or condition being treated, or to otherwise provide a desired pharmacological and/or physiologic effect.

"MARCE" refers to "Major Adverse Renal and Cardiac Event" defined as one or more of cardiovascular death, non-fatal myocardial infarction, or non-fatal stroke, heart failure, need for renal replacement therapy, hospitalizations for cardiac or renal reasons, sustained reduction in eGFR of >25%, prolonged hospitalization or re-hospitalization events "Pharmaceutically acceptable" refers to molecular entities and compositions that are "generally regarded as safe"— e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s)

and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Co-administered with", administered "in combination with", "a combination of" or "administered along with" may be used interchangeably and mean that two or more agents are administered in the course of therapy. The agents may be administered together at the same time or separately in spaced apart intervals. The agents may be administered in a single dosage form or in separate dosage forms.

"Contrast agents" or "contrast media" include, but are not limited to, iodine, barium, gadolinium. For example, Iodine-based and barium-sulfate compounds are commonly used in x-ray and computed tomography (CT) imaging exams. The methods described herein may be used with any procedure that uses a contrast agent, including, but not limited to x-ray-based imaging, magnetic resonance imaging, cardiac procedures, imaging of the digestive system including computed tomography scans, Angiography (arterial investigations), Venography (venous investigations), VCUG (voiding cystourethrography), HSG (hysterosalpingogram) and IVU (intravenous urography).

As used herein, the term "prevention" or "preventing" means to administer a composition to a subject or a system at risk for or having a predisposition for one or more symptoms caused by a disease or disorder to facilitate cessation of a particular symptom of the disease or disorder, a reduction or prevention of one or more symptoms of the disease or disorder, a reduction in the severity of the disease or disorder, the complete ablation of the disease or disorder, stabilization or delay of the epileptic or progression of the disease or disorder.

"Prodrug", as used herein, refers to a pharmacological substance (drug) that is administered to a subject in an inactive (or significantly less active) form. Once administered, the prodrug is metabolized in the body (in vivo) into a compound having the desired pharmacological activity.

"Analog" and "Derivative" are used herein interchangeably and refer to a compound that possesses the same core as the parent compound, but may differ from the parent compound in bond order, the absence or presence of one or more atoms of atoms, and combinations thereof. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

"Stereoisomer", as used herein, refers to isomeric molecules that have the same molecular formula and sequence of bonded atoms (constitution), but which differ in the three dimensional orientations of their atoms in space. Examples of stereoisomers include enantiomers and diastereomers. As used herein, an enantiomer refers to one of the two mirror-image forms of an optically active or chiral molecule. Diastereomers (or diastereoisomers) are stereoisomers that are not enantiomers (non-superimposable mirror images of each other). Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Enantiomers and/or diasteromers can be resolved or separated using techniques known in the art. "Chirality" also includes axial and planar chirality.

The term "pharmaceutically acceptable salt", as used herein, refers to derivatives of the compounds defined herein, wherein the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

EXAMPLES

The examples provided herein are included solely for augmenting the disclosure herein and should not be considered to be limiting in any respect.

Example 1

The following prophetic Example may be used to assess the impact of trimetazidine on the prevention of contrast induced acute acute kidney injury in high-risk patients undergoing percutaneous coronary intervention or peripheral transluminal angioplasty. This multicenter, randomized, double blind, placebo-controlled study may be used to evaluate the efficacy of trimetazidine in reducing the incidence of CI-AKI among high-risk patients undergoing planned percutaneous coronary intervention (PCI) or peripheral transluminal angioplasty (PTA). In addition, this study may be used to determine the efficacy of trimetazidine in reducing the incidence of adverse clinical events (death, RRT, MI, stroke, clinically driven revascularization or major adverse cardiovascular events) at 30 days among high-risk patients undergoing planned PCI or PTA. This study may also be optionally used to determine the efficacy of trimetazidine in reducing the incidence of adverse clinical events (death, RRT, MI, stroke, clinically driven revascularization or major adverse cardiovascular events) at 90 days among high-risk patients undergoing planned PCI or PTA. In addition, this study may optionally be used to determine the efficacy of trimetazidine in reducing the incidence of adverse clinical events (death, RRT, MI, stroke, clinically driven revascularization or major adverse cardiovascular events) at one year among high-risk patients undergoing planned PCI or PTA.

The primary efficacy endpoint of this study may include the incidence of CI-AKI at 72 hours post contrast media exposure. CI-AKI may be defined as an increase in serum creatinine of more than 0.5 mg/dl (44.2 µmol/L) or a percentage increase in serum creatinine equal to or greater than 50% from the baseline blood draw prior to contrast media exposure. The primary efficacy endpoint may include the composite occurrence of adverse clinical events at 30 days including death, RRT, MI, stroke, clinically driven revascularization or major adverse cardiovascular events. Additional efficacy endpoints may optionally include the composite occurrence of adverse clinical events at 90 days including death, RRT, MI, stroke, clinically driven revascularization or major adverse cardiovascular events. Additional efficacy endpoints may optionally include the composite occurrence of adverse clinical events at one year including death, RRT, MI, stroke, clinically driven revascularization or major adverse cardiovascular events.

Secondary endpoints may include one or more of the following clinical events within 30 days: All-cause mortality; myocardial infarction; dialysis-dependent renal failure; unplanned re-hospitalization; repeat coronary revascularization of the target lesion; major bleeding (not related to coronary bypass procedures); major adverse cardiovascular events and stroke. Additional secondary endpoint may include the following laboratory-based metrics at 72 hours: percent of subjects with SCr increase of >0.5 mg/dl (44.2 µmol); percent of subjects with SCr increase of >25%; percent of subjects with SCr increase >100%; percent of subjects with SCr increase >200%; and mean change in eGFR.

Example 2

The following prophetic Example may be used to assess the impact of trimetazidine reduce the risk of contrast-induced acute kidney injury (CI-AKI) and associated major adverse renal and cardiac events (MARCE). This multi-center, randomized, double blind, placebo-controlled study may be used to evaluate the proportion of subjects who experience any adverse renal and cardiac event (MARCE) over the 90-day period after the day of contrast procedure between trimetazidine and placebo groups. MARCE is defined as cardiovascular death, non-fatal myocardial infarction, heart failure, need for renal replacement therapy, hospitalizations for cardiac or renal reasons and a reduction in eGFR of ≥25%. Additional outcome measures may include the difference between subjects treated with trimetazidine and placebo in one or more of the following: (1) the incidence of CI-AKI based upon the KDIGO definition of CI-AKI; (2) total number of MARCE events, since each subject may experience multiple events; (3) Proportion of subjects who experience cardiovascular death; (4) Proportion of subjects who experience non-fatal myocardial infarction; (5) Proportion of subjects who experience heart failure; (6) Proportion of subjects who need for renal replacement therapy; (7) Days out of hospital and alive; (8) Proportion of subjects who are re-hospitalized for cardiac or renal reasons; (9) Proportion of subjects with sustained reduction in eGFR of >25% at 90 days; and/or (10) change from baseline in QoL of subjects.

Within approximately 48 hours before the estimated start of the angiography (e.g., arterial sheath insertion), trimetazidine may be administered for a planned range of, e.g., 3-6 doses on a planned schedule. Administration may be continued for up to 120 days, e.g., 90 days, from the date of the procedure depending on results observed during follow-up visits. For example, follow-up may occur after 1, 2, 4, 7, 30, 60, 90 or 120 days. Subjects may have one or more of the following criteria: An eGFR <45 mL/min and >15 mL/min as determined by the Modification of Diet in Renal Disease (MDRD) equation or an eGFR <60 mL/min and ≥45 mL/min as determined by the MDRD equation and diabetes mellitus, congestive heart failure or anemia.

Example 3

The following prophetic Example may be used to assess the impact of trimetazidine reduce the risk of contrast-induced acute kidney injury (CI-AKI) and associated major adverse renal and cardiac events (MARCE). This multi-center, randomized, double blind, placebo-controlled study may be used to evaluate the efficacy of trimetazidine on the reduction of major adverse renal and cardiac events (MARCE), prevention of contrast-induced acute kidney injury (CI-AKI) and/or to assess the efficacy of trimetazidine on the reduction of individual components of MARCE. Primary outcome measures may include determining the difference in time to first major adverse renal and cardiac event (MARCE) over a period of time (e.g., a 90-day period) after the day of contrast procedure between trimetazidine and placebo. Another outcome measure may include the difference between subjects treated with trimetazidine and placebo in: (1) the incidence of CI-AKI based upon the KDIGO definition of CI-AKI from baseline to the end of treatment (e.g., day 90); (2) Proportion of subjects who experience any MARCE events; (3) the total number of MARCE events, since each subject may experience multiple events; (4) time to cardiovascular death; (5) time to non-fatal myocardial infarction; (6) time to non-fatal stroke; (7) time to heart failure; (8) time to need for renal replacement therapy; (9) duration of index hospitalization; (10) days out of hospital and alive; (11) proportion of subjects with sustained reduction in eGFR of >20%; (12) proportion of subjects with prolonged hospitalization or re-hospitalization events; and/or (13) time to re-hospitalization for cardiac or renal reasons. During this prospective study subjects may receive either daily administration of trimetazidine (e.g., 20 mg three times daily) or placebo. During index hospitalization, all patients would receive intravenous isotonic crystalloid solution (normal saline or sodium bicarbonate) according to good clinical practice. Within approximately 48 hours before the estimated start of, e.g., angiography, trimetazidine may be administered for a planned range of 3-6 doses (e.g., 20 mg three times daily for one to two days). The study subjects may then continue to receive trimetazidine for a treatment period (e.g., an additional 90 days) from the date of the index procedure. One or more outcome measures may be evaluated at intervals between study start and total treatment time, e.g., after 1, 2, 4, 7, 14, 30, 60 and/or 90 days.

Those skilled in the art will recognize, or be able to ascertain using no more than routine experimentation, many equivalents to the embodiments and examples described herein. Such equivalents are intended to be encompassed by the claims.

The invention claimed is:

1. A protocol to effect reduction of further impairment of kidney function in a subject who exhibits pre-existing impaired kidney function, which protocol comprises administering an effective amount of trimetazidine (TMZ) or pharmaceutically acceptable salt thereof to said subject prior to said subject undergoing a procedure that employs intravascular contrast media wherein said TMZ or pharmaceutically acceptable salt thereof is administered within 12 hours prior to start of said procedure and is continued for at least about 5 days after said procedure has been performed on said subject.

2. The protocol of claim 1 which further includes measuring at least one component of Major Adverse Renal and Cardiac Events (MARCE) during a period of time subsequent to said procedure.

3. The protocol of claim 2 wherein MARCE includes at least one of cardiovascular death, non-fatal myocardial infarction, non-fatal stroke, heart failure, need for renal replacement therapy, hospitalizations for cardiac reasons, hospitalizations for renal reasons, prolonged hospitalization, and re-hospitalization events.

4. The protocol of claim 2 wherein one of said components is sustained reduction of eGFR.

5. The protocol of claim 2 wherein said component is measured multiple times during a period of time subsequent to said procedure.

6. The protocol of claim 1 wherein prior to the administration of TMZ or pharmaceutically acceptable salt thereof said subject has been identified as having impaired kidney function by determining eGFR.

7. The protocol of claim 1 wherein said subject is determined to have an eGFR of between about 15-90 ml/min/1.73 m$^2$.

8. The protocol of claim 7 wherein said eGFR has been determined to be between about 15-60 ml/min/1.73 m$^2$.

9. The protocol of claim 1 wherein trimetazidine or pharmaceutically acceptable salt thereof is administered for at least about 30, 45, 60, 75, or 90 days after said procedure.

10. The protocol of claim 1 wherein trimetazidine or pharmaceutically acceptable salt thereof is administered within about 6, 5, 4, 3, 2, or 1 hour(s) before said procedure.

11. The protocol of claim 1 wherein the further impairment of kidney function is acute kidney injury.

12. The protocol of claim 1 wherein the further impairment of kidney function is chronic kidney disease.

13. The protocol of claim 1 wherein administration of trimetazidine or pharmaceutically acceptable salt thereof is parenteral or oral.

* * * * *